(12) United States Patent
Shimizu et al.

(10) Patent No.: US 8,338,161 B2
(45) Date of Patent: Dec. 25, 2012

(54) LACTIC ACID BACTERIA

(75) Inventors: Kanetada Shimizu, Zama (JP); Tomoko Yaeshima, Yamato (JP)

(73) Assignee: Morinaga Milk Industry Co., Ltd., Tokyo (JP)

(*) Notice: Subject to any disclaimer, the term of this patent is extended or adjusted under 35 U.S.C. 154(b) by 804 days.

(21) Appl. No.: 12/162,705

(22) PCT Filed: Nov. 2, 2007

(86) PCT No.: PCT/JP2007/071395
§ 371 (c)(1),
(2), (4) Date: Jul. 30, 2008

(87) PCT Pub. No.: WO2008/099544
PCT Pub. Date: Aug. 21, 2008

(65) Prior Publication Data
US 2010/0086988 A1 Apr. 8, 2010

(30) Foreign Application Priority Data
Feb. 13, 2007 (JP) .................. 2007-032645

(51) Int. Cl.
*C12N 1/20* (2006.01)
(52) U.S. Cl. ..................... 435/252.1; 424/93.4
(58) Field of Classification Search .................. None
See application file for complete search history.

(56) References Cited

FOREIGN PATENT DOCUMENTS

| EP | 0 974 268 A1 | 1/2000 |
|---|---|---|
| EP | 974268 | * 1/2000 |
| EP | 1443105 | 8/2004 |
| EP | 1900285 A1 | 3/2008 |
| EP | 1989942 | 11/2008 |
| FR | 2842707 | * 7/2003 |
| JP | 10-229819 | 9/1998 |
| JP | 2002-335860 | 11/2002 |
| JP | 2003-250528 | 9/2003 |
| JP | 2004-018469 | 1/2004 |
| NZ | 569737 | 11/2011 |
| WO | 2006/129508 A1 | 7/2006 |

OTHER PUBLICATIONS

Doleyres et al., Biotechnol. Prog. 2004, 20, 145-150.*
Official Action issued in New Zealand Patent Application No. 569590, dated Nov. 8, 2011, 2 pages.
Office Action for Canadian Patent Application No. 2,656,916 mailed Jan. 17, 2011, 3 pages.
Hiromi Kimoto et al., Survival of lactococci during passage through mouse digestive tract, Canadian Journal of Microbiology, (2003), pp. 707-711, vol. 49.
European Patent Office, European Search Report in Application No. 07831129.7-2405, dated Feb. 24, 2010.
European Patent Office, Search Report and Written Opinion in International Patent Application No. PCT/JP2007/071395 dated Nov. 27, 2007.
Office Action issued in Philippine Patent Application No. 12008501601, dated Apr. 2, 2012, 2 pages.

* cited by examiner

*Primary Examiner* — Irene Marx
(74) *Attorney, Agent, or Firm* — Wood, Herron & Evans, LLP

(57) ABSTRACT

The present invention relates to bacteria of a genus *Lactococcus* having bacteriological properties of: (1) fermentability which curdles a 10% (W/W) reconstituted skim milk medium when cultivated at a temperature of 25° C. to 37° C. for 16 hours; (2) *Bifidobacterium longum* growth-promoting properties which lead to a viable count of *Bifidobacterium longum* of $5 \times 10^8$ CFU/g or more, when co-cultivated with *Bifidobacterium longum* in the 10% (W/W) reconstituted skim milk medium, until the pH thereof is 4.4 to 4.6; and (3) *Bifidobacterium longum* survivability-improving properties during storage, which lead to a survival rate of *Bifidobacterium longum* of 30% or more, after co-cultivation with *Bifidobacterium longum* in the 10% (W/W) reconstituted skim milk medium until the pH thereof is 4.4 to 4.6, rapid cooling, and two weeks storage at 10° C.

6 Claims, No Drawings

LACTIC ACID BACTERIA

TECHNICAL FIELD

The present invention relates to novel lactic acid bacteria belonging to the genus *Lactococcus*, bacterial powders containing the lactic acid bacteria, a pharmaceutical composition containing the lactic acid bacteria, an intestinal function-controlling agent containing the lactic acid bacteria, and a method for promoting growth of *Bifidobacterium longum* and improving survivability thereof using the lactic acid bacteria.

Priority is claimed on Japanese Patent Application No. 2007-032645, filed on Feb. 13, 2007, the contents of which are incorporated herein by reference.

BACKGROUND ART

It is known that lactic acid bacteria such as bacteria of the genus *Lactococcus* or bacteria of the genus *Bifidobacterium* (hereinafter, abbreviated to "*Bifidobacterium*") have an intestinal function-regulating activity, immuno-stimulating activity, and anti-cancer activity. Accordingly, lactic acid bacteria tend to be often formulated in food in accordance with an increase of health consciousness of consumers. In particular, *Bifidobacterium* such as *Bifidobacterium longum* is one of the predominant bacterial strains in intestinal microflora formed in the human intestinal tract, and demands for fermented milk or other food products containing viable *Bifidobacterium* are increasing.

*Bifidobacterium* exhibits a poor proliferation potency in milk medium. Accordingly, various growth-stimulating substances are generally formulated in fermented milk so that *Bifidobacterium* is contained therein at a constant content, such as $1 \times 10^7$ CFU/ml. However, the growth-stimulating substances are generally expensive and may deteriorate taste. In addition, preservation of *Bifidobacterium* under acidic conditions is difficult and tends to result in death thereof. Thus, the viable count of *Bifidobacterium* in fermented milk products decreases with accelerating speed during distribution of the fermented milk products.

Accordingly, it is expected that a growth promotion of *Bifidobacterium* or an improvement of survivability thereof during storage will enable not only preparation of fermented milk containing a large amount of viable *Bifidobacterium*, but also preparation of fermented milk keeping an abundant amount of viable *Bifidobacterium* from immediately after preparation until being consumed.

Various methods for promoting growth of *Bifidobacterium* or improving the survivability thereof during storage by fermentation with *Bifidobacterium* and another lactic acid bacterium without adding any growth-stimulating substances or the like have been disclosed. For example, (1) yogurt containing *Lactococcus lactis* subsp. *lactis*, *Lactococcus lactis* subsp. *cremoris*, and *Bifidobacterium*, and a method for preparing the yogurt has been disclosed (see, for example, Patent Document 1), as a method for promoting growth of *Bifidobacterium* to prepare fermented milk.

For example, (2) a method for fermenting milk with *Bifidobacterium*, including cultivating *Bifidobacterium breve* together with *Lactococcus lactis* subsp. *lactis*, which forms neither diacetyl nor acetoin, on a medium containing milk as the main component thereof has been disclosed (see, for example, Patent Document 2), as a method for improving the survivability of *Bifidobacterium* during storage of fermented milk.

Patent Document 1: Japanese Patent Publication No. 3,364,491.
Patent Document 2: Japanese Patent Publication No. 3,068,484.

DISCLOSURE OF THE INVENTION

[Problems to be Solved by the Invention]

Although the growth of *Bifidobacterium* is promoted and the fermentation time is shortened in accordance with the above-mentioned method (1), there is no disclosure with respect to the survivability of *Bifidobacterium* during storage in Patent Document 1. In contrast, although both growth-stimulating effects and survivability-improving effects are recognized by using a mixture composed of a specific *Bifidobacterium* and a specific lactic acid bacterium in accordance with the above-mentioned method (2), there is no disclosure with respect to *Bifidobacterium* other than *Bifidobacterium breve*, such as *Bifidobacterium longum*, which is generally formulated in food.

The present invention has for an object thereof the provision of lactic acid bacteria which stimulate the growth of *Bifidobacterium*, preferably *Bifidobacterium longum*, and improve the survivability thereof during storage.

The present invention has also for an object thereof the provision of bacterial powders containing the lactic acid bacteria, a pharmaceutical composition containing the lactic acid bacteria, an intestinal function-controlling agent containing the lactic acid bacteria, and a method for promoting growth of *Bifidobacterium longum* and improving survivability thereof using the lactic acid bacteria.

[Means for Solving the Problems]

The inventors of the present invention intensively investigated so as to solve the above-mentioned problems, and performed a fermentation test by co-cultivation with *Bifidobacterium longum* to find lactic acid bacterial strains which exhibit excellent fermentability in 10% (W/W) reconstituted skim milk medium. As a result, the inventors found lactic acid bacterium strains which can promote the growth of *Bifidobacterium longum* to a viable count of $5 \times 10^8$ CFU/g when the pH is 4.4 to 4.6, and enhance the survival rate of *Bifidobacterium longum* to 30% or more after the end of fermentation, rapid cooling, and two weeks storage at 10° C. Thus, the inventors completed the present invention.

That is, the present invention provides bacteria of a genus *Lactococcus* having the following bacteriological properties:
(1) fermentability which curdles a 10% (W/W) reconstituted skim milk medium when cultivated at a temperature of 25° C. to 37° C. for 16 hours;
(2) *Bifidobacterium longum* growth-promoting properties which lead to a viable count of *Bifidobacterium longum* of $5 \times 10^8$ CFU/g or more, when co-cultivated with *Bifidobacterium longum* in the 10% (W/W) reconstituted skim milk medium until the pH thereof is 4.4 to 4.6; and
(3) *Bifidobacterium longum* survivability-improving properties during storage, which lead to a survival rate of *Bifidobacterium longum* of 30% or more, after co-cultivation with *Bifidobacterium longum* in the 10% (W/W) reconstituted skim milk medium until the pH thereof is 4.4 to 4.6, rapid cooling, and two weeks storage at 10° C.

The present invention also provides the bacteria of the genus *Lactococcus* characterized in that the bacteria have no ability to ferment xylose and produce neither diacetyl nor acetoin.

The present invention also provides the bacteria of the genus *Lactococcus*, in which the bacteria are *Lactococcus lactis* subsp. *lactis*.

The present invention also provides the bacteria of the genus *Lactococcus*, in which at least one bacterial strain of the *Bifidobacterium longum* is selected from the group consisting of *Bifidobacterium longum* FERM BP-7787 and *Bifidobacterium longum*-type strain ATCC 15707.

The present invention also provides the bacteria of the genus *Lactococcus*, in which the bacteria are *Lactococcus lactis* subsp. *lactis* MCC852 (FERM BP-10742).

The present invention also provides the bacteria of the genus *Lactococcus*, in which the bacteria are *Lactococcus lactis* subsp. *lactis* MCC857 (FERM BP-10757).

The present invention also provides the bacteria of the genus *Lactococcus*, in which the bacteria are *Lactococcus lactis* subsp. *lactis* MCC859 (FERM BP-10744).

The present invention also provides the bacteria of the genus *Lactococcus*, in which the bacteria are *Lactococcus lactis* subsp. *lactis* MCC865 (FERM BP-10745).

The present invention also provides the bacteria of the genus *Lactococcus*, in which the bacteria are *Lactococcus lactis* subsp. *lactis* MCC866 (FERM BP-10746).

The present invention also provides bacterial powders containing any of the above-mentioned bacteria of the genus *Lactococcus*.

The present invention also provides a pharmaceutical composition containing any of the above-mentioned bacteria of the genus *Lactococcus*.

The present invention also provides any of the above-mentioned bacteria of the genus *Lactococcus*.

The present invention also provides a method for promoting growth of *Bifidobacterium longum* and improving survivability thereof, including using any of the above-mentioned bacteria of the genus *Lactococcus*.

[Effects of the Invention]

The bacteria of the genus *Lactococcus* according to the present invention, and the method for promoting growth of *Bifidobacterium longum* and improving the survivability thereof according to the present invention realize significant improvement of the growth of *Bifidobacterium longum* and the survivability thereof during storage, and therefore fermented milk products containing a large amount of *Bifidobacterium longum* are more efficiently produced than before. In addition, the viable count of *Bifidobacterium longum* in fermented milk products is kept at a sufficient level even during distribution. The thus provided fermented milk products exhibit high intestinal function-regulating effects and are useful for health control.

BEST MODE FOR CARRYING OUT THE INVENTION

Bacteria of a genus *Lactococcus*, particularly *Lactococcus lactis* subsp. *lactis*, according to the present invention have the properties (1), (2), and (3).

The property (1) relates to fermentability. If lactic acid bacteria can rapidly proliferate and have a strong fermentability sufficient to curdle a 10% (W/W) reconstituted skim milk medium when cultivated therein at a temperature between 25° C. and 37° C. for 16 hours, the lactic acid bacteria can effectively promote the growth of *Bifidobacterium longum* when fermented milk is prepared. As used herein, the phrase "curdle a culture medium." refers to a phenomenon in which pH of the culture medium decreases below an isoelectric point of a milk protein thereof by acid fermentation, and thereby the milk protein agglomerates and the culture medium is curdled. The "10% (W/W) reconstituted skim milk medium" may be prepared, for example, by dissolving 10% by mass of skim milk powders (manufactured by MORINAGA MILK INDUSTRY CO., LTD., for example) in water.

Although the temperature range suitable for fermentation with bacteria of the genus *Lactococcus* is generally between 20° C. and 30° C., the bacteria of the genus *Lactococcus* according to the present invention exhibit a strong fermentability at a temperature between 25° C. and 37° C. In other words, the bacteria of the genus *Lactococcus* according to the present invention exhibit a sufficient fermentability within a temperature range suitable for fermentation with *Bifidobacterium longum* (30° C. to 40° C.).

The property (2) relates to *Bifidobacterium longum* growth-promoting properties. A milk medium such as a 10% (W/W) reconstituted skim milk medium exhibits excellent taste, mouth-feeling, and external appearance, when the pH thereof is approximately 4.6, casein and other components contained therein are generally precipitated, and the culture medium is wholly curdled. Accordingly, fermentation is generally stopped by rapidly cooling or the like when the pH reaches approximately 4.6, to prepare fermented milk products. Therefore, the lactic acid bacteria having the growth-promoting properties that can lead to the viable count of *Bifidobacterium longum* being a high count of $5 \times 10^8$ CFU/g or more when co-cultivated with *Bifidobacterium longum* in the 10% (W/W) reconstituted skim milk medium until the pH thereof is 4.4 to 4.6 can effectively increase the viable count of *Bifidobacterium longum* in fermented milk at the time of preparation of fermented milk.

The property (3) relates to *Bifidobacterium longum* survivability-improving properties during storage. The quality preservation period of fermented milk products is generally about two weeks when stored at 10° C. or lower. Accordingly, fermented milk which maintains a sufficient viable count of *Bifidobacterium longum* even on an end point of the quality preservation period thereof can be produced, provided that the lactic acid bacteria have the survivability-improving properties during storage that can lead to the survival rate of *Bifidobacterium longum* being 30% or more after co-cultivation with *Bifidobacterium longum* in the 10% (W/W) reconstituted skim milk medium until the pH thereof is 4.4 to 4.6, rapid cooling, and two weeks storage at 10° C.

The bacteria of the genus *Lactococcus* according to the present invention may be prepared in accordance with the following method, for example. First, bacterial strains are isolated from various samples, and strains which exhibit excellent fermentability in the 10% (W/W) reconstituted skim milk medium, more specifically fermentability sufficient to curdle the 10% (W/W) reconstituted skim milk medium when cultivated therein at a temperature of 25 to 37° C. for 16 hours, are selected from the isolated bacterial strains. Then, the selected bacterial strains are co-cultivated with *Bifidobacterium longum*, and bacterial strains which have *Bifidobacterium longum* growth-promoting properties and survivability-improving properties during storage defined as the above-mentioned properties (2) and (3) are selected. It is preferable that bacterial strains which do not have an ability to ferment xylose and produce neither diacetyl nor acetoin be further selected.

In the following, the present invention will be explained in more detail.

1. Isolation of Bacterial Strains

In order to isolate bacterial strains having the above-mentioned properties from the natural world, the present inventors collected samples from the natural world in Japan, diluted the samples with an anaerobic dilution buffer ("The World of Enterobacteria" published by Soubunsha Co., Ltd., written by Tomotari Mitsuoka, Page 322, 1980: hereinafter, abbreviated to "Reference 1"), inoculated the diluted samples on each plate of Briggs liver broth (see the above-mentioned Reference 1, Page 319), and then cultured the inoculated samples at 30° C. under anaerobic conditions. Among the thus obtained colonies, bacterial strains which showed morphological characteristics of streptococcal bacteria and were recognized as Gram-positive bacteria by microscopic observation of applied specimens were picked up. The picked up strains were each streak-inoculated on each BL agar flat plate and then repeatedly cultivated under anaerobic conditions in the same manner as described above to obtain purely isolated bacterial strains. The isolated bacterial strains were subjected to a fermentation test on a 10% (W/W) reconstituted skim milk medium as described below to obtain 20 bacterial strains with fermentability defined as the above-mentioned property (1). Then, the obtained bacterial strains were co-cultured with. *Bifidobacterium longum* to obtain 5 bacterial strains having both the growth-promoting properties which raise the viable count of *Bifidobacterium longum* at pH of 4.4 to 4.6 to $5 \times 10^8$ CFU/g or more and the survivability-improving properties during storage which raise the survival rate of *Bifidobacterium longum* to 30% or more when stored at 10° C. for two weeks after rapid cooling at pH of 4.4 to 4.6. The 5 bacterial strains are named as "MCC852", "MCC857", "MCC859", "MCC865", and "MCC866", respectively.

2. Bacteriological Properties

The bacteriological properties of the 5 bacterial strains will be shown in the following. The tests for determining the bacteriological properties were performed with reference to Bergey's Manual of Systematic Bacteriology, edited by Peter H. A. Sneath, Vol. 2, published by Williams and Wilkins Company, 1986).

(I) Bacterial morphology (observed through an optical microscope after anaerobic cultivation on a BL agar flat plate at 30° C. for 72 hours)
  Size: 1 to 2 µm (diameter)
  Morphology: Streptococcal bacteria
(II) Gram staining: Positive
(III) Litmus milk: Curdled
(IV) Endospore formation: Negative
(V) Gas production from glucose: Negative
(VI) Motility: Negative
(VII) Catalase activity: Negative
(VIII) Arginine decarboxylase test: Positive
(IX) Gas production from citric acid: Negative
(X) Temperature susceptibility (at 60° C. for 30 minutes and at 65° C. for 30 minutes): Positive in both cases
(XI) Glucose degradation product: L-lactic acid

TABLE 1

| | Bacterial strain | | MCC 852 | MCC 857 | MCC 859 | MCC 865 | MCC 866 | ATCC 19435 |
|---|---|---|---|---|---|---|---|---|
| XII | Growth temperature | 10° C. | +S | +S | + | +S | +S | +S |
| | | 40° C. | + | + | + | + | + | + |
| | | 45° C. | − | − | − | − | − | − |
| XIII | Salt resistance | 2% | + | + | + | + | + | + |
| | | 3% | + | + | + | + | + | + |
| | | 4% | + | + | + | + | + | + |
| | | 6.5% | (+)S | − | − | (+)S | (+)S | − |
| XIV | pH resistance | 9.2 | + | + | + | + | + | + |
| | | 9.6 | +S | + | + | + | − | − |
| XV | Methylene blue resistance | 0.01% | + | + | + | + | + | + |
| | | 0.1% | + | + | + | + | + | + |
| | | 0.3% | ± | +S | + | +S | + | − |
| XVI | Producibiliry of ammonia from arginine | | + | + | + | + | ± | + |
| XVII | Sugar fermentation | Arabinose | − | − | − | − | − | − |
| | | Xylose | − | − | − | − | − | + |
| | | Rhamnose | − | − | − | − | − | − |
| | | Ribose | + | + | +S | + | + | + |
| | | Glucose | + | + | + | + | + | + |
| | | Mannose | + | + | + | + | + | + |
| | | Fructose | + | + | + | + | + | + |
| | | Galactose | + | + | + | + | + | + |
| | | Sucrose | − | − | − | − | − | − |
| | | Maltose | + | + | + | + | + | + |
| | | Cellobiose | + | + | + | + | + | + |
| | | Lactose | + | + | + | + | + | + |
| | | Trehalose | + | + | + | + | + | + |
| | | Melibiose | − | − | − | − | − | − |
| | | Raffinose | − | − | − | − | − | − |
| | | Melezitose | − | − | − | − | − | − |
| | | Dextrin | + | + | + | + | + | + |
| | | Starch | +S | + | − | + | + | ±S |
| | | Glycogen | − | − | − | − | − | − |
| | | Inulin | − | − | − | − | − | − |
| | | Mannitol | (+)S | + | + | − | − | − |
| | | Sorbitol | − | − | − | − | − | − |
| | | Inositol | − | − | − | − | − | − |
| | | Esculin | + | + | (+)S | + | + | +S |
| | | Salicin | + | + | +S | + | + | + |
| | | Amygdalin | − | ± | − | (+)S | (+)S | − |
| | | Methyl glucoside | − | − | − | − | − | − |
| | | Sodium gluconate | − | ± | + | − | − | − |

+: Positive.
(+): Slightly-positive.
±: Extremely slightly-positive.
−: Negative.
s: Slow reaction.

The above-mentioned bacteriological properties (I) to (XI) are common to all of the 5 bacterial strains and the *Lactococcus lactis* subsp. *lactis*-type strain ATCC 19435. The growth temperature (XII), the salt-resistance (XIII), the pH-resistance (XIV), the methylene blue-resistance (XV), the producibility of ammonia from arginine (XVI), and the sugar fermentability (XVII) of each strain are shown in Table 1. The sugar fermentation was examined with respect to 28 kinds of sugar using a medium for sugar fermentation disclosed by Mitsuoka (Tomotari Mitsuoka, The bacteriology of lactic acid bacteria", Clinical Examination 18, Pages 1163 to 1172, 1974).

It is apparent from the above-mentioned results that all of the 5 bacterial strains have the bacteriological properties common to *Lactococcus lactis* subsp. *lactis* bacterial strains. Thus, the 5 bacterial strains have been recognized to be *Lactococcus lactis* subsp. *lactis* bacterial strains. On the other hand, it is apparent from the above-mentioned bacteriological properties (XII) to (XVII) that the 5 bacterial strains are different from the *Lactococcus lactis* subsp. *lactis*-type strain in that the 5 bacterial strains do not have any abilities to ferment xylose.

The 5 bacterial strains were deposited by the applicant at the International Patent Organism Depositary, National Institute of Advanced Industrial Science and Technology, (Central 6, 1-1, Higashi 1-Chome Tsukuba-shi, Ibaraki-ken, JAPAN (postal code number: 305-8566)) as novel bacterial strains. The accession number of the *Lactococcus lactis* subsp. *lactis* MCC852 is FERM BP-10742, that of the *Lactococcus lactis* subsp. *lactis* MCC857 is FERM BP-10757, that of the *Lactococcus lactis* subsp. *lactis* MCC859 is FERM BP-10744, that of the *Lactococcus lactis* subsp. *lactis* MCC865 is FERM BP-10745, and that of the *Lactococcus lactis* subsp. *lactis* MCC866 is FERM BP-10746. The *Lactococcus lactis* subsp. *lactis* MCC852, 859, 865, and 866 were deposited on Dec. 1, 2006, and the *Lactococcus lactis* subsp. *lactis* MCC857 was deposited on Jan. 10, 2007.

3. Test with Respect to Fermentability on 10% (W/W) Reconstituted Skim Milk Medium.

A 10% (W/W) reconstituted skim milk medium prepared by dissolving skim milk powders (manufactured by MORINAGA MILK INDUSTRY CO., LTD.) in water was sterilized at 95° C. for 30 minutes. Each 3% (V/V) bacterial strain starter was inoculated into the reconstituted skim milk medium, and then cultured at 25, 30, or 37° C. for 16 hours. After the obtained culture medium was rapidly cooled, the curdled state was observed, and the pH and the viable count of the contained lactic acid bacteria were measured. The viable count was measured using commercially available BCP plate count agar (manufactured by Eiken. Chemical Co., LTD.) flat plates. The measurement results are shown in Table 2.

*Lactococcus lactis* subsp. *lactis*-type strain ATCC 19435 disclosed in Patent Document 2 was used as a control strain.

TABLE 2

| Bacterial strain | at 25° C. for 16 hours | | | Culture condition at 30° C. for 16 hours | | | at 37° C. for 16 hours | | |
|---|---|---|---|---|---|---|---|---|---|
| | Viable count (CFU/g) | pH | | Viable count (CFU/g) | pH | | Viable count (CFU/g) | pH | |
| MCC852 | $2.0 \times 10^8$ | 4.53 | Curdled | $1.5 \times 10^9$ | 4.44 | Curdled | $8.0 \times 10^8$ | 4.63 | Curdled |
| MCC857 | $1.7 \times 10^9$ | 4.53 | Curdled | $1.5 \times 10^9$ | 4.41 | Curdled | $1.1 \times 10^9$ | 4.5 | Curdled |
| MCC859 | $1.4 \times 10^9$ | 4.54 | Curdled | $8.5 \times 10^8$ | 4.44 | Curdled | $8.1 \times 10^8$ | 4.59 | Curdled |
| MCC865 | $2.0 \times 10^9$ | 4.52 | Curdled | $1.5 \times 10^9$ | 4.42 | Curdled | $8.8 \times 10^8$ | 4.63 | Curdled |
| MCC866 | $2.0 \times 10^9$ | 4.52 | Curdled | $1.3 \times 10^9$ | 4.4 | Curdled | $8.5 \times 10^8$ | 4.61 | Curdled |
| ATCC 19435 | $5.2 \times 10^8$ | 5.93 | Uncurdled | $4.4 \times 10^8$ | 5.65 | Uncurdled | $3.2. \times 10^8$ | 5.51 | Uncurdled |

When each bacterial strain of *Lactococcus lactis* subsp. *lactis* MCC852, 857, 859, 865, and 866, that is, the bacteria of the genus *Lactococcus* according to the present invention, was used, pH of the culture medium was decreased to 4.4 to 4.6 under all temperature conditions, and the culture medium was curdled. In addition, the viable count of the contained lactic acid bacteria was approximately $1 \times 10^9$ CFU/g, and thus favorable proliferation and fermentability conditions were recognized.

On the other hand, when the *Lactococcus lactis* subsp. *lactis*-type strain ATCC 19435 was used, pH of the culture medium was 5.5 or more and the culture medium was not curdled under any temperature conditions. In addition, the viable count of the lactic acid bacteria was significantly less at 30° C. or higher, particularly, than that of the bacteria of the genus *Lactococcus* according to the present invention.

4. Co-cultivation Test with *Bifidobacterium longum*
(1) Co-cultivation Test with *Bifidobacterium longum* FERM BP-7787.

*Lactococcus lactis* subsp. *lactis*-type strain ATCC 19435 was used as a control strain.

First, each culture of the 5 bacterial strains (*Lactococcus lactis* subsp. *lactis* MCC852, 857, 859, 865, and 866) and *Bifidobacterium longum* FERM BP-7787 was prepared in accordance with a method described in the following Example 1.

The *Bifidobacterium longum* FERM BP-7787 was accepted by the International Patent Organism Depositary, National Institute of Advanced Industrial Science and Technology, (Central 6, 1-1, Higashi 1-Chome Tsukuba-shi, Ibaraki-ken, JAPAN (postal code number: 305-8566)) on Oct. 31, 2001.

In addition, 1,000 mL of a 10% (W/W) reconstituted skim milk medium containing 0.2% (W/W) yeast extract (manufactured by Difco) was sterilized at 90° C. for 30 minutes. Then, 30 mL of a culture of the *Lactococcus lactis* subsp. *lactis*-type strain ATCC 19435 was inoculated into the reconstituted skim milk medium, and cultivated at 30° C. for 16 hours to prepare a culture of the *Lactococcus lactis* subsp. *lactis*-type strain ATCC 19435.

1% (V/V) of each culture of the *Lactococcus lactis* subsp. *lactis* strains prepared as above was inoculated with 1% (V/V) of the culture of the *Bifidobacterium longum* FERM BP-7787 into a 10% (W/W) reconstituted skim milk medium sterilized at 90° C. for 10 minutes, and the mixture were cultivated at 37° C. for 16 hours to obtain fermented milk. The fermented milk was rapidly cooled and the pH thereof and the viable count of the contained *Bifidobacterium longum* were measured. Then, the resultant was further stored at 10° C. for two weeks, and the viable count of the *Bifidobacterium longum* was measured at one week and two weeks after initiation of storage. The viable count of the *Bifidobacterium longum* was measured using TOS propionate agar (manufactured by YAKULT PHARMACEUTICAL INDUSTRY CO., LTD.) flat plates. The measurement results are shown in Table 3.

TABLE 3

| Bacterial strain | Viable count of *Bifidobacterium* (CFU/g) | | | pH |
|---|---|---|---|---|
| | Immediately after end of fermentation | After one week storage | After two weeks storage | Immediately after end of fermentation |
| MCC852 | $5.7 \times 10^8$ | $5.5 \times 10^8$ | $5.5 \times 10^8$ | 4.52 |
| MCC857 | $8.0 \times 10^8$ | $7.5 \times 10^8$ | $6.5 \times 10^8$ | 4.47 |
| MCC859 | $6.8 \times 10^8$ | $6.9 \times 10^8$ | $5.7 \times 10^8$ | 4.55 |
| MCC865 | $8.3 \times 10^8$ | $8.0 \times 10^8$ | $7.3 \times 10^8$ | 4.56 |
| MCC866 | $6.4 \times 10^8$ | $6.3 \times 10^8$ | $5.3 \times 10^8$ | 4.42 |
| ATCC19435 | $1.2 \times 10^8$ | pH was 5 or more and storage test could not be performed. | | |

Each fermented milk prepared by using the *Lactococcus lactis* subsp. *lactis* MCC852, 857, 859, 865, or 866 had a pH of approximately 4.5 and a *Bifidobacterium longum* viable count of $5 \times 10^8$ CFU/g or more after fermentation. When every fermented milk was stored at 10° C. for two weeks, the survival rate of *Bifidobacterium longum* was 80% or more.

On the other hand, milk fermentation did not proceed with the *Lactococcus lactis* subsp. *lactis*-type strain ATCC 19435, and pH of the fermented milk was 5.0 or more and storage thereof at 10° C. was impossible. In addition, the *Bifidobacterium longum* viable count immediately after end of fermentation was approximately $1 \times 10^8$ CFU/g, which was significantly small in comparison with the case where the bacteria of the genus *Lactococcus* according to the present invention were used.

Thus, it is apparent that the 5 bacterial strains (the *Lactococcus lactis* subsp. *lactis* MCC852, 857, 859, 865, and 866) excellently promote the growth of the *Bifidobacterium longum* FERM BP-7787 and enhance the survival rate thereof during storage in comparison with other known bacterial strains belonging to the *Lactococcus lactis* subsp. *lactis*.

It is also apparent that the case where *Bifidobacterium longum* is co-cultured with the *Lactococcus lactis* subsp. *lactis* that forms neither diacetyl nor acetoin as described in Patent Document 2 is unlike the case where *Bifidobacterium breve* is used, and neither such *Bifidobacterium longum*-proliferation promoting effects nor -survivability improving effects as those disclosed in Patent Document 2 are exhibited.

(2) Co-cultivation Test with *Bifidobacterium longum*-type Strain ATCC 15707

The *Bifidobacterium longum* growth-promoting properties of the bacteria of the genus *Lactococcus* according to the present invention and *Bifidobacterium longum* survivability-improving properties thereof during storage were checked using the *Bifidobacterium longum* FERM BP-7787 and the *Bifidobacterium longum*-type strain ATCC 15707.

First, a culture of the *Lactococcus lactis* subsp. *lactis* MCC857 and a culture of the *Bifidobacterium longum* FERM BP-7787 were prepared in accordance with a method described in the following Example 1.

In addition, a mixed culture of *Streptococcus thermophilus* and *Lactobacillus bulgaricus* was prepared in accordance with a method described in the following Example 21.

In addition, an 11% (W/W) skim milk medium containing 0.2% (W/W) yeast extract was sterilized at 90° C. for 30 minutes. Then, 10% (V/V) of the *Bifidobacterium longum*-type strain ATCC 15707 was inoculated as a starter into the skim milk medium, and cultivated at 37° C. until the pH reached 4.6 to prepare a culture of the *Bifidobacterium longum*-type strain ATCC 15707.

1% (V/V) of the culture of the *Lactococcus lactis* subsp. *lactis* MCC857 prepared as described above, either 1% (V/V) of the culture of the *Bifidobacterium longum* FERM BP-7787 or 1% (V/V) of the culture of the *Bifidobacterium longum*-type strain ATCC 15707, and 0.01% (V/V) of the mixed culture of *Streptococcus thermophilus* and *Lactobacillus bulgaricus* were inoculated into a 10% (W/W) reconstituted skim milk medium sterilized at 90° C. for 10 minutes, and cultivated at 37° C. until pH reached 4.6 to obtain fermented milk. After the obtained fermented milk was rapidly cooled, the viable count of *Bifidobacterium longum* was measured. In addition, the fermented milk was stored at 10° C. for two weeks, and the viable count of *Bifidobacterium longum* was measured at one week or two weeks after initiation of storage.

On the other hand, either 1.5% (V/V) of the culture of the *Bifidobacterium longum* FERM BP-7787 prepared as described above or 1.5% (V/V) of the culture of the *Bifidobacterium longum*-type strain ATCC 15707, and 0.4% (V/V) of the mixed culture of *Streptococcus thermophilus* and *Lactobacillus bulgaricus* were inoculated into a 10% (W/W) reconstituted skim milk medium sterilized at 90° C. for 10 minutes, and cultivated at 37° C. until pH reached 4.6 to obtain fermented milk as a control. The viable *Bifidobacterium longum* count in the fermented milk was measured in the same manner. The measurement results are shown in Table 4.

TABLE 4

| MCC857 | *Bifidobacterium longum* | *Bifidobacterium* viable count (CFU/g) | | |
|---|---|---|---|---|
| | | Immediately after end of fermentation | After one week storage | After two weeks storage |
| Presence | FERM BP-7787 | $1.0 \times 10^9$ | $1.0 \times 10^9$ | $7.1 \times 10^8$ |
| Presence | ATCC 15707 | $6.5 \times 10^8$ | $3.8 \times 10^8$ | $2.0 \times 10^8$ |
| Absence | FERM BP-7787 | $2.0 \times 10^8$ | $1.9 \times 10^8$ | $4.0 \times 10^7$ |
| Absence | ATCC 15707 | $3.0 \times 10^7$ | $1.1 \times 10^6$ | Undetectable |

Both viable counts of the *Bifidobacterium longum* FERM BP-7787 and the *Bifidobacterium longum*-type strain ATCC 15707 in fermented milk were significantly increased by co-cultivating with the *Lactococcus lactis* subsp. *lactis* MCC857. In addition, the survival rate of every *Bifidobacterium longum* stored at 10° C. for two weeks was 30% or more: that of the *Bifidobacterium longum* FERM BP-7787 was 71% and that of the *Bifidobacterium longum*-type strain ATCC 15707 was 31%.

In contrast, the survival rate of the *Bifidobacterium longum* FERM BP-7787 stored at 10° C. for two weeks after cultivating in the absence of *Lactococcus lactis* subsp. *lactis* MCC857 was 20% and no viable *Bifidobacterium longum*-type strain ATCC 15707 stored at 10° C. for two weeks after cultivating in the absence of *Lactococcus lactis* subsp. *lactis* MCC857 was detected.

The same results were obtained when every *Lactococcus lactis* subsp. *lactis* MCC852, 859, 865, and 866 was used instead of the *Lactococcus lactis* subsp. *lactis* MCC857.

Thus, it is apparent that every *Lactococcus lactis* subsp. *lactis* MCC852, 857, 859, 865, and 866 has both excellent properties for promoting the growth of *Bifidobacterium longum* strains other than *Bifidobacterium longum* FERM BP-7787 having an excellent survivability during storage and properties for improving the survivability of *Bifidobacterium longum* strains other than *Bifidobacterium longum* FERM BP-7787 during storage.

5. Comparative Test with Mixture of *Lactococcus lactis* subsp. *lactis* and *Lactococcus lactis* subsp. *cremoris* disclosed in Patent Document 1.

The culture of *Lactococcus lactis* subsp. *lactis* MCC857, the culture of *Bifidobacterium longum*-type strain ATCC 15707, and the mixed culture of *Streptococcus thermophilus* and *Lactobacillus bulgaricus* were prepared in accordance with the method described in the above 4(2).

1% (V/V) of the culture of *Lactococcus lactis* subsp. *lactis* MCC857, 1% (V/V) of the culture of *Bifidobacterium longum*-type strain ATCC 15707, and 0.01% (V/V) of the mixed culture of *Streptococcus thermophilus* and *Lactobacillus bulgaricus*, as prepared in the above manner, were inoculated into a 10% (W/W) reconstituted skim milk medium sterilized at 90° C. for 10 minutes. The mixture was cultivated at 37° C. until pH reached 4.6 to prepare fermented milk. The fermented milk was rapidly cooled and the viable count of the contained *Bifidobacterium longum* was measured.

In contrast, 1% (V/V) of the culture of *Bifidobacterium longum*-type strain ATCC 15707 prepared in the above-manner, and 2% (V/V) of mixture "EZAL MA14" composed of *Lactococcus lactis* subsp. *lactis* and *Lactococcus lactis* subsp. *cremoris* (manufactured by Rhodia) were inoculated into a 10% (W/W) reconstituted skim milk medium sterilized at 90° C. for 10 minutes, as a control. The mixture was cultivated at 38° C. until pH reached 4.6 to prepare fermented milk. The viable count of *Bifidobacterium longum* in the fermented milk was measured. The mixture "EZAL MA14" corresponds to a product "EZAL MR014" (manufactured by Rhodia) described in Patent Document 1.

The *Bifidobacterium longum* count in fermented milk prepared using *Lactococcus lactis* subsp. *lactis* MCC857 was $5.5 \times 10^8$ CFU/g. In contrast, no viable *Bifidobacterium longum* was detected in a diluted solution obtained by diluting fermented milk prepared using the mixture "EZAL MA14" by $10^6$ fold, and thus the viable count of *Bifidobacterium longum* present in the fermented milk was revealed to be $1 \times 10^6$ CFU/g or less.

In other words, it was revealed that neither effects of promoting the growth of *Bifidobacterium* nor effects of shortening fermentation time, as mentioned in Patent Document 1, were achieved when *Bifidobacterium longum* was co-cultivated with *Lactococcus lactis* subsp. *lactis* and *Lactococcus lactis* subsp. *cremoris*.

As described above, the bacteria of the genus *Lactococcus* according to the present invention exhibit strong fermentability in the 10% (W/W) reconstituted skim milk medium at a temperature suitable to fermentation with *Bifidobacterium*. In addition, when the bacteria of the genus *Lactococcus* are co-cultivated with *Bifidobacterium longum*, the bacteria of the genus *Lactococcus* exhibit excellent effects of promoting growth of *Bifidobacterium longum* and excellent effects of improving survivability thereof during storage, and have the properties which are not accompanied with conventionally known bacterial strains belonging to the genus *Lactococcus*. In addition, the bacteria of the genus *Lactococcus* can efficiently produce fermented products such as fermented milk due to the extremely strong fermentability thereof. In addition, it is expected that fermented products with favorable taste can be produced by the bacteria of the genus *Lactococcus*, since the bacteria of the genus *Lactococcus* produce neither diacetyl nor acetoin.

In particular, the 5 bacterial strains (*Lactococcus lactis* subsp. *lactis* MCC852, 857, 859, 865, and 866) can be safely formulated in various foods or drinks such as fermented food products, since the 5 bacterial strains were selected from lactic acid bacteria isolated from the natural world in terms of favorable fermentability and possession of *Bifidobacterium longum* growth-promotion properties and *Bifidobacterium longum* survivability-improving properties during storage.

The bacteria of the genus *Lactococcus* according to the present invention may be used in the form of bacterial powders in the same manner as that of other lactic acid bacteria. The bacterial powders may be formulated in food or feed.

The bacteria of the genus *Lactococcus* according to the present invention may also be preferably formulated in a pharmaceutical composition such as an intestinal function-controlling agent. In the case where the bacteria of the genus *Lactococcus* according to the present invention are formulated in an intestinal function-controlling agent, the content of the bacteria of the genus *Lactococcus* or the daily dosage thereof is not particularly limited, provided that the content or the daily dosage is estimated to be sufficient to exhibit intestinal function-controlling effects. It is preferable, for example, that the daily ingested amount of the bacteria of the genus *Lactococcus* be approximately $1 \times 10^9$ CFU.

Although a preculture medium used for cultivating *Bifidobacterium longum* and the bacteria of the genus *Lactococcus* in advance is not particularly limited provided that the preculture medium is usually used, the preculture medium is preferably a milk medium. The preculture medium is more preferably a reconstituted skim milk medium, since the reconstituted skim milk medium is easily handled. It is preferable that the concentration of the reconstituted skim milk medium be 3% (W/W) or more, and more preferably 8% (W/W) or more. In addition, the preculture medium may contain growth-stimulating substances such as yeast extract or reducing agents such as L-cysteine. It is particularly preferable that a growth-stimulating substance be formulated in the preculture medium, since *Bifidobacterium* exhibits a low level of proliferation in the milk medium. Specifically, a culture medium containing 0.1 to 1% (W/W) of yeast extract may be used. The preculture medium is subjected to sterilization for the use. The sterilization may be performed in accordance with a conventional method, specifically performed by heating at 80 to 122° C. for 5 to 40 minutes, preferably at 85 to 95° C. for 5 to 35 minutes.

The growth of *Bifidobacterium longum* and the survivability thereof during storage can be simply and efficiently improved in accordance with the method for promoting growth of *Bifidobacterium longum* and improving survivability thereof according to the present invention. Specifically, the bacteria of the genus *Lactococcus* according to the present invention and *Bifidobacterium longum* are co-cultivated in accordance with the method. Although the inoculation ratio of *Bifidobacterium longum* to the bacteria of the genus *Lactococcus* according to the present invention to be co-cultured as starters in a base medium is not particularly limited, the inoculation ratio is preferably 100:1 to 1:10, and more preferably 10:1 to 1:1. Although the amount thereof to be inoculated in the base medium is not particularly limited, it is preferable that the total amount of *Bifidobacterium longum* and the bacteria of the genus *Lactococcus* inoculated be 0.01 to 10% (V/V), more preferably 0.1 to 5% (V/V), with respect to the amount of the base medium.

Although the base medium is not particularly limited, provided that the base medium is usually used for co-cultivating *Bifidobacterium* with lactic acid bacteria, it is preferable that the base medium contain milk as the main component thereof. In accordance with the method for promoting the growth of *Bifidobacterium longum* and improving the survivability thereof according to the present invention, the proliferation of *Bifidobacterium longum* and the survivability thereof can be improved even in such a milk medium which is usually unsuitable for *Bifidobacterium* growth. The base medium may be prepared by formulating a sweetener such as sucrose, pectin, fruit, fruit juice, agar, gelatin, oil and fat, flavor, coloring agent, stabilizer, reducing agent, or the like, in cow's milk, skim milk, fresh cream, butter, whole milk powder, powdered skim milk, or the like, as needed, followed by sterilizing, homogenizing, cooling, and the like. It is particularly preferable that the base medium be used for preparing fermented milk containing *Bifidobacterium longum*.

In the following, the present invention will be circumstantially explained by indicating some examples. However, the present invention is not limited to the following examples.

EXAMPLE 1

30 mL of a seed culture of *Lactococcus lactis* subsp. *lactis* MCC852 was inoculated into 1000 ml of 10% (W/W) reconstituted skim milk medium sterilized at 90° C. for 30 minutes, and then cultivated at 25° C. for 16 hours. On the other hand, 1000 ml of 11% (W/W) skim milk medium containing 0.2% (W/W) yeast extract was sterilized at 90° C. for 30 minutes, and 100 mL of a seed culture of *Bifidobacterium longum* FERM BP-7787 was inoculated into the skim milk medium, followed by cultivating at 37° C. for 6 hours.

Apart from the above, 50 L of a base medium prepared by mixing and dissolving raw materials composed of powdered skim milk, whole milk powder, pectin, and sucrose, the base medium containing 0.5% (W/W) of butterfat, 8.0% (W/W) of nonfat milk solid component, 5.0% (W/W) of sucrose, and 0.2% (W/W) of pectin, was sterilized at 90° C. for 10 minutes, followed by cooling at 40° C. 50 mL of the above-obtained culture of the *Lactococcus lactis* subsp. *lactis* MCC852 precultured and 500 mL of the above-obtained culture of *Bifidobacterium longum* FERM BP-7787 precultured were inoculated into the sterilized base medium, followed by cultivating at 37° C. for 16 hours to obtain fermented milk. The fermented milk was immediately cooled while stirring, and the cooled fermented milk was homogenized at a pressure of 15 MPa, followed by putting the resultant into a glass container having a 200 mL capacity and then sealing the container to obtain yogurt drink. The obtained yogurt drink had a pH of 4.64, and contained $6.8 \times 10^8$ CFU/g of *Bifidobacterium longum*. When the yogurt drink was stored at 10° C. for 14 days, the viable count of *Bifidobacterium longum* was $5.8 \times 10^8$ CFU/g, and the survival rate thereof was 85%.

EXAMPLE 2

Yogurt drink was obtained in the same manner as that of Example 1, except that *Lactococcus lactis* subsp. *lactis* MCC857 was used instead of *Lactococcus lactis* subsp. *lactis* MCC852. The obtained yogurt drink had a pH of 4.62 and contained $8.5 \times 10^8$ CFU/g of *Bifidobacterium longum*. When the yogurt drink was stored at 10° C. for 14 days, the viable count of *Bifidobacterium longum* was $7.6 \times 10^8$ CFU/g, and the survival rate thereof was 89%.

EXAMPLE 3

Yogurt drink was obtained in the same manner as that of Example 1, except that *Lactococcus lactis* subsp. *lactis* MCC859 was used instead of *Lactococcus lactis* subsp. *lactis* MCC852. The obtained yogurt drink had a pH of 4.56 and contained $7.2 \times 10^8$ CFU/g of *Bifidobacterium longum*. When the yogurt drink was stored at 10° C. for 14 days, the viable count of *Bifidobacterium longum* was $5.8 \times 10^8$ $_{CFU}$/g, and the survival rate thereof was 81%.

EXAMPLE 4

Yogurt drink was obtained in the same manner as that of Example 1, except that *Lactococcus lactis* subsp. *lactis* MCC865 was used instead of *Lactococcus lactis* subsp. *lactis* MCC852. The obtained yogurt drink had a pH of 4.54 and contained $6.9 \times 10^8$ CFU/g of *Bifidobacterium longum*. When the yogurt drink was stored at 10° C. for 14 days, the viable count of *Bifidobacterium longum* was $6.6 \times 10^8$ CFU/g, and the survival rate thereof was 96%.

EXAMPLE 5

Yogurt drink was obtained in the same manner as that of Example 1, except that *Lactococcus lactis* subsp. *lactis* MCC866 was used instead of *Lactococcus lactis* subsp. *lactis* MCC852. The obtained yogurt drink had a pH of 4.55 and contained $6.5 \times 10^8$ CFU/g of *Bifidobacterium longum*. When the yogurt drink was stored at 10° C. for 14 days, the viable count of *Bifidobacterium longum* was $6.2 \times 10^8$ CFU/g, and the survival rate thereof was 95%.

EXAMPLE 6

500 mL of a seed culture of *Lactococcus lactis* subsp. *lactis* MCC852 cultivated at 37° C. for 16 hours in a culture medium composed of 50 g of meat extract, 100 g of yeast extract, 100 g of peptone, 200 g of lactose, 50 g of $K_2HPO_4$, 10 g of $KH_2PO_4$, 4 g of cystin, and 9.5 L of water, was inoculated into 10L of a culture medium having the same composition as that of the above-mentioned culture medium, and then cultivated at 37° C. for 16 hours. In addition, the thus obtained whole culture liquid (10.5 L) was inoculated into 200 L of a culture medium sterilized at 90° C. for 30 minutes having the same composition as that of the above-mentioned culture medium, and then cultivated at 37° C. for 16 hours. The viable count after cultivation was $3.0 \times 10^9$ CFU/ml.

Then, bacterial cells were collected by centrifugation (15,000 rpm) using a sharpless type centrifugal device (manufactured by TOMY SEIKO CO., LTD., under the trade name of RD-20IV), and suspended again in physiological saline (sterilized at 90° C. for 30 minutes) in the same amount as that of the culture medium, followed by centrifuging as described above to collect the bacterial cells again. The collected bacterial cells were suspended in 20 L of a solution (sterilized at 90° C. for 30 minutes) containing 10% (W/W) of skim milk, 1% (W/W) of sucrose, and 1% (W/W) of monosodium glutamate, and freeze-dried in accordance with a conventional method to obtain about 2.2 kg of powder containing $8.6 \times 10^{10}$ CFU/g of *Lactococcus lactis* subsp. *lactis* MCC852.

EXAMPLE 7

About 2.2 kg of powder containing $9.2 \times 10^{10}$ CFU/g of *Lactococcus lactis* subsp. *lactis* MCC857 was obtained in the same manner as that of EXAMPLE 6 except that *Lactococcus lactis* subsp. *lactis* MCC857 was used instead of *Lactococcus lactis* subsp. *lactis* MCC852.

EXAMPLE 8

About 2.2 kg of powder containing $8.5 \times 10^{10}$ CFU/g of *Lactococcus lactis* subsp. *lactis* MCC859 was obtained in the same manner as that of EXAMPLE 6 except that *Lactococcus lactis* subsp. *lactis* MCC859 was used instead of *Lactococcus lactis* subsp. *lactis* MCC852.

EXAMPLE 9

About 2.2 kg of powder containing $9.4 \times 10^{10}$ CFU/g of *Lactococcus lactis* subsp. *lactis* MCC865 was obtained in the same manner as that of EXAMPLE 6 except that *Lactococcus lactis* subsp. *lactis* MCC865 was used instead of *Lactococcus lactis* subsp. *lactis* MCC852.

EXAMPLE 10

About 2.2 kg of powder containing $8.8 \times 10^{10}$ CFU/g of *Lactococcus lactis* subsp. *lactis* MCC866 was obtained in the same manner as that of EXAMPLE 6 except that *Lactococcus lactis* subsp. *lactis* MCC866 was used instead of *Lactococcus lactis* subsp. *lactis* MCC852.

EXAMPLE 11

About 20 kg of an intestinal function-controlling agent containing bacterial powder of *Lactococcus lactis* subsp. *lactis* MCC852 was obtained by uniformly mixing 20 g of bacterial powder containing *Lactococcus lactis* subsp. *lactis* MCC852, the bacterial powder being prepared in EXAMPLE 6, with 14 kg of dry-sterilized starch and 6 kg of lactose.

EXAMPLE 12

About 20 kg of an intestinal function-controlling agent containing bacterial powder of *Lactococcus lactis* subsp. *lactis* MCC857 was obtained by uniformly mixing 20 g of bacterial powder containing *Lactococcus lactis* subsp. *lactis* MCC857, the bacterial powder being prepared in EXAMPLE 7, with 14 kg of dry-sterilized starch and 6 kg of lactose.

EXAMPLE 13

About 20 kg of an intestinal function-controlling agent containing bacterial powder of *Lactococcus lactis* subsp. *lactis* MCC859 was obtained by uniformly mixing 20 g of bacterial powder containing *Lactococcus lactis* subsp. *lactis* MCC859, the bacterial powder being prepared in EXAMPLE 8, with 14 kg of dry-sterilized starch and 6 kg of lactose.

EXAMPLE 14

About 20 kg of an intestinal function-controlling agent containing bacterial powder of *Lactococcus lactis* subsp. *lactis* MCC865 was obtained by uniformly mixing 20 g of bacterial powder containing *Lactococcus lactis* subsp. *lactis* MCC865, the bacterial powder being prepared in EXAMPLE 9, with 14 kg of dry-sterilized starch and 6 kg of lactose.

EXAMPLE 15

About 20 kg of an intestinal function-controlling agent containing bacterial powder of *Lactococcus lactis* subsp. *lactis* MCC866 was obtained by uniformly mixing 20 g of bacterial powder containing *Lactococcus lactis* subsp. *lactis* MCC866, the bacterial powder being prepared in EXAMPLE 10, with 14 kg of dry-sterilized starch and 6 kg of lactose.

EXAMPLE 16

30 mL of a seed culture of *Lactococcus lactis* subsp. *lactis* MCC852 was inoculated into 1000 mL of 10% (W/W) reconstituted skim milk medium sterilized at 90° C. for 30 minutes, and then cultivated at 25° C. for 16 hours.

Apart from the above, 50 L of raw milk composed of 3.0% (W/W) of butterfat, and 9.5% (W/W) of nonfat milk solid component was heated at 70° C., homogenized at a pressure of 15 MPa, sterilized at 90° C. for 10 minutes, and then cooled at 40° C. After 500 mL of culture of *Lactococcus lactis* subsp. *lactis* MCC852 precultured as described above was inoculated into the sterilized base medium, and then put into a resin container having a 500 mL capacity, the container was sealed. The culture was cultivated at 37° C. for 16 hours, and then immediately cooled. The thus obtained fermented milk had a pH of 4.70 and contained $1.3 \times 10^9$ CFU/g of lactic acid bacteria.

EXAMPLE 17

Fermented milk was obtained in the same manner as that of Example 16, except that *Lactococcus lactis* subsp. *lactis* MCC857 was used instead of *Lactococcus lactis* subsp. *lactis* MCC852. The obtained fermented milk had a pH of 4.69 and contained $1.5 \times 10^9$ CFU/g of lactic acid bacteria.

EXAMPLE 18

Fermented milk was obtained in the same manner as that of Example 16, except that *Lactococcus lactis* subsp. *lactis* MCC859 was used instead of *Lactococcus lactis* subsp. *lactis* MCC852. The obtained fermented milk had a pH of 4.65 and contained $1.4 \times 10^9$ CFU/g of lactic acid bacteria.

EXAMPLE 19

Fermented milk was obtained in the same manner as that of Example 16, except that *Lactococcus lactis* subsp. *lactis* MCC865 was used instead of *Lactococcus lactis* subsp. *lactis* MCC852. The obtained fermented milk had a pH of 4.64 and contained $1.5 \times 10^9$ CFU/g of lactic acid bacteria.

EXAMPLE 20

Fermented milk was obtained in the same manner as that of Example 16, except that *Lactococcus lactis* subsp. *lactis* MCC866 was used instead of *Lactococcus lactis* subsp. *lactis* MCC852. The obtained fermented milk had a pH of 4.62 and contained $1.3 \times 10^9$ CFU/g of lactic acid bacteria.

EXAMPLE 21

30 mL of a seed culture of *Lactococcus lactis* subsp. *lactis* MCC852 was inoculated into 1000 mL of a 10% (W/W) reconstituted skim milk medium sterilized at 90° C. for 30 minutes, and then cultivated at 25° C. for 16 hours. Apart form the above, 50 mL of a mixed culture of *Streptococcus thermophilus* (manufactured by HANSEN) and *Lactobacillus bulgaricus* (manufactured by HANSEN) was inoculated into 1500 ml of a 10% (W/W) reconstituted skim milk medium sterilized at 90° C. for 30 minutes, and then cultivated at 37° C. for 5 hours.

Apart from the above, 50 L of raw milk containing 3.0% (W/W) of butterfat and 9.0% (W/W) of nonfat milk solid component was heated at 70° C., homogenized at a pressure of 15 MPa, sterilized at 90° C. for 10 minutes, and then cooled at 40° C. 500 mL of the culture of *Lactococcus lactis* subsp. *lactis* MCC852 precultured as described above and 50 mL of a mixed culture of *Streptococcus thermophilus* and *Lactobacillus bulgaricus* were inoculated into the sterilized base medium, and then put into a resin container having a 500 mL capacity. After the container was sealed, the bacteria were cultivated at 37° C. for 7 hours, and then immediately cooled. The thus obtained fermented milk had a pH of 4.75 and contained $9.8 \times 10^8$ CFU/g of lactic acid bacteria.

EXAMPLE 22

Fermented milk was obtained in the same manner as that of EXAMPLE 21 except that *Lactococcus lactis* subsp. *lactis* MCC857 was used instead of *Lactococcus lactis* subsp. *lactis* MCC852. The obtained fermented milk had a pH of 4.74 and contained $1.2 \times 10^9$ CFU/g of lactic acid bacteria.

EXAMPLE 23

Fermented milk was obtained in the same manner as that of EXAMPLE 16 except that *Lactococcus lactis* subsp. *lactis* MCC859 was used instead of *Lactococcus lactis* subsp. *lactis* MCC852. The obtained fermented milk had a pH of 4.70 and contained $1.6 \times 10^9$ CFU/g of lactic acid bacteria.

EXAMPLE 24

Fermented milk was obtained in the same manner as that of EXAMPLE 16 except that *Lactococcus lactis* subsp. *lactis* MCC865 was used instead of *Lactococcus lactis* subsp. *lactis* MCC852. The obtained fermented milk had a pH of 4.72 and contained $1.7 \times 10^9$ CFU/g of lactic acid bacteria.

EXAMPLE 25

Fermented milk was obtained in the same manner as that of EXAMPLE 16 except that *Lactococcus lactis* subsp. *lactis* MCC866 was used instead of *Lactococcus lactis* subsp. *lactis* MCC852. The obtained fermented milk had a pH of 4.70 and contained $1.5 \times 10^9$ CFU/g of lactic acid bacteria.

INDUSTRIAL APPLICABILITY

The bacteria of the genus *Lactococcus* according to the present invention enable *Bifidobacterium longum* in a fermented milk product such as yogurt, yogurt drink, acidic milk drink, or the like, to maintain a high level of viable count and survival rate during storage, and therefore the bacteria of the genus *Lactococcus* are useful in terms of health control and fermented milk production, and can be applied in the field of manufacturing fermented milk products.

The invention claimed is:
1. An isolated bacterial strain selected from the group consisting of *Lactococcus lactis* subsp. *lactis* MCC852 (FERM BP-10742), *Lactococcus lactis* subsp. *lactis* MCC857 (FERM BP-10757), *Lactococcus lactis* subsp. *lactis* MCC859 (FERM BP-10744), *Lactococcus lactis* subsp. *lactis* MCC865 (FERM BP-10745), and *Lactococcus lactis* subsp. *lactis* MCC866 (FERM BP-10746).
2. The isolated bacterial strain according to claim 1, which is *Lactococcus lactis* subsp. *lactis* MCC852 (FERM BP-10742).
3. The isolated bacterial strain according to claim 1, which is *Lactococcus lactis* subsp. *lactis* MCC857 (FERM BP-10757).
4. The isolated bacterial strain according to claim 1, which is *Lactococcus lactis* subsp. *lactis* MCC859 (FERM BP-10744).
5. The isolated bacterial strain according to claim 1, which is *Lactococcus lactis* subsp. *lactis* MCC865 (FERM BP-10745).
6. The isolated bacterial strain according to claim 1, which is *Lactococcus lactis* subsp. *lactis* MCC866 (FERM BP-10746).

* * * * *